United States Patent [19]
Deiss et al.

[11] Patent Number: 6,057,111
[45] Date of Patent: May 2, 2000

[54] GENE IDENTIFICATION METHOD

[75] Inventors: Louis Paul Deiss; Fruma Yehiely; Elena Efimova, all of Chicago; Nora Cecilia Vasquez-Iaslop, Oak Park, all of Ill.; Paz Einat, Nes Ziona, Israel

[73] Assignee: Quark Biotech, Inc., Pleasanton, Calif.

[21] Appl. No.: 09/284,782

[22] PCT Filed: Nov. 12, 1997

[86] PCT No.: PCT/US97/20989

§ 371 Date: Jul. 6, 1999

§ 102(e) Date: Jul. 6, 1999

[87] PCT Pub. No.: WO98/21366

PCT Pub. Date: May 22, 1998

Related U.S. Application Data

[60] Provisional application No. 60/030,549, Nov. 13, 1996.
[51] Int. Cl.[7] .................................................. C12Q 1/68
[52] U.S. Cl. ................................ 435/6; 435/29; 435/320.1
[58] Field of Search ................................. 435/6, 29, 320.1

[56] References Cited

PUBLICATIONS

Deiss et al. Identification of a novel serine/threonine kinase and a novel 15–kD protein as potential mediatiors of a gamma interferon–induced cell death. Genes & Development vol. 9 pp. 15–30, 1995.

*Primary Examiner*—John S. Brusca
*Attorney, Agent, or Firm*—Kohn & Associates

[57] ABSTRACT

A method for the identification of genes that are essential for the maintenance of specific cell phenotypes is disclosed. The method includes the initial step of identifying a cell type with a phenotype of interest. Gene inactivation is performed on an aliquot of cells of the cell type of interest. Positive selection is then performed to an aliquot of the cell culture to which gene inactivation has been applied. Cells which continue to maintain the phenotype following gene inactivation have not had the gene of interest inactivated whereas cells in which genes necessary for maintaining the phenotype have been inactivated have been lost. Utilizing subtraction analysis between treated and untreated aliquots the gene in the cells which has been inactivated that affects the phenotype of interest is identified. Genes that are identified by the method are also disclosed as well as antibodies directed against the gene product of the identified genes. Further a customized kit for the practice of the gene identification method is also disclosed.

7 Claims, 2 Drawing Sheets

GENE IDENTIFICATION METHOD

This application claims benefit of provisional 60/030,549 filed Nov. 13, 1996.

BACKGROUND OF THE INVENTION

1. Field of the Invention

The present invention relates to a method of identifying genes, specifically genes that maintain specific cell phenotypes.

2. Description of Related Art

There are methods available to isolate and identify specific genes. However these methods are not efficient and rapid. Applicant has previous disclosed the Technical Knock Out (TKO) selection method which has the advantage of rapid isolation of genes that inhibit proliferation in a specified restrictive environment [Deiss and Kimchi, 1991; Deiss et al, 1995; Kissil et al, 1995; Deiss et al, 1996]. However, this method has the limitation of requiring a phenotype that can be efficiently selected against, such as a cell growth arrest or cell killing phenotype.

Recently Smith et al [1995] and U.S. Pat. No. 5,612,180 have described a method called genetic footprinting to identify genes. The method involves mutagenesis of potentially large numbers of genes followed by a genetic selection of the cells containing the mutated genes. This is followed by retrospective analysis of the effect of individual gene inactivation on the behavior cells containing these inactivations. From this information new genes are determined. This method has significant disadvantages for large scale gene identification. The genetic footprinting method involves mutagenesis by gene insertion and because of this requires a haploid target which imposes a limitation on the method. Second, the method of determining the effect of each gene inactivation on the fitness of the cells containing the mutation involves a PCR amplification of the target gene which requires prior knowledge of the nucleotide sequence of all the target genes that will be studied which limits the gene base which can be searched. It would be useful to have a method which does not require a haploid target and does not require a known sequence.

It would be useful to have a rapid method which can identify genes to be isolated that are essential for the maintenance of specific cell phenotypes where positive selection exists for the phenotypes. These identified genes are excellent targets for the development of pharmacological inhibitors which would also act clinically to inhibit the specific phenotype. In other words it would be useful to have a tool which can effectively identify pharmacological targets for inhibition of deleterious phenotypes.

SUMMARY OF THE INVENTION

According to the present invention, a method for the identification of genes that are essential for the maintenance of specific cell phenotypes is disclosed. The method includes the initial step of identifying a cell type with a phenotype of interest. The method allows the phenotype of interest to be phenotypes relating to growth, phenotypes relating to release of factors and phenotypes relating to other basic cell functions.

Gene inactivation is performed on an aliquot of cells of the cell type of interest. Possible methods of gene inactivation include Genetic Suppressor Element (GSE) inactivation, Random Homozygous Knock-Out (RHKO) inactivation, or Technical Knock Out (TKO) inactivation.

Positive selection is then performed on an aliquot of the cell culture to which gene inactivation has been applied. The positive selection includes manipulations that test the ability of cells to survive under specific culture conditions, ability to express a specific factor, changes in cell structure, or differential gene expression.

Cells which continue to maintain the phenotype following gene inactivation have not had the gene of interest inactivated whereas cells in which genes necessary for maintaining the phenotype have been inactivated have been lost. Utilizing subtraction analysis between treated and untreated aliquots the gene in the cells which has been inactivated that affects the phenotype of interest is identified. The subtraction analysis can include the methods of differential display, representational differential analysis (RDA), suppressive subtraction hybridization (SSH), serial analysis of gene expression (SAGE), gene expression microarray (GEM), nucleic acid chip technology, or direct sequencing.

The invention further discloses the genes that are identified by the method of the present invention and for antibodies directed against the gene product of these identified genes. The present invention also provides for a customized kit to practice the method of the present invention.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
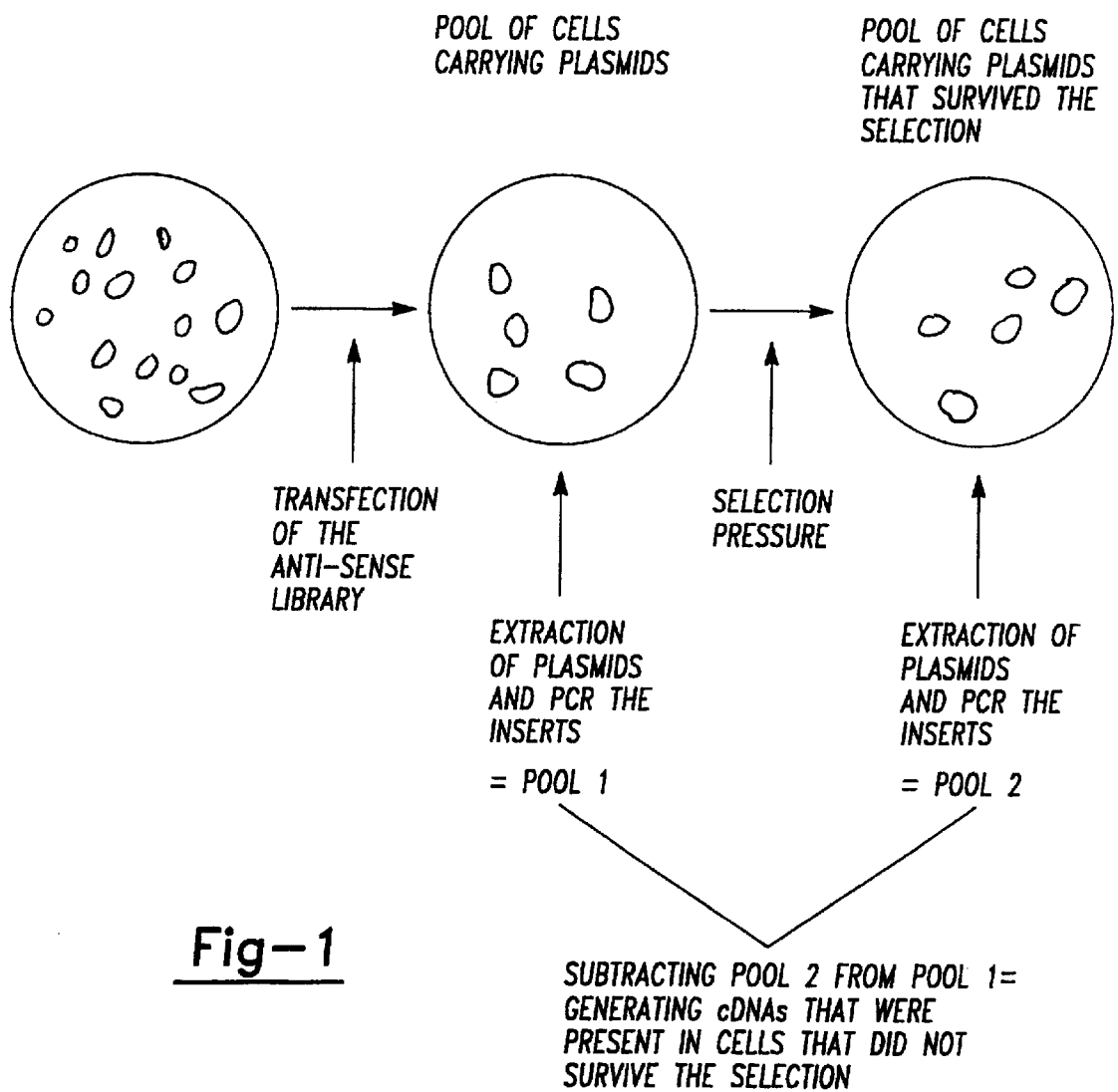
FIG. 1 is a schematic representation of a general outline of the method of the present invention.

According to the present invention, a method for the identification of which genes are essential for the maintenance of a specific cell phenotype is disclosed. Phenotypes that can be studied are those for which changes can be monitored in either haploid or diploid cells. The method requires two general steps. The first is the inactivation of genes in the cell by any method known in the art and then in the second applying positive selection for the phenotype of interest followed by the identification via a subtraction analysis of the gene in the cells which has been inactivated that affects the phenotype of interest. By this method, a collection of genes that are essential for the maintenance of a specific phenotype are identified at the conclusion of the procedure. The invention further discloses the genes that are identified by the method of the present invention and for antibodies directed against the gene product of these identified genes.

Briefly, the method includes initially the identification of a cell type for which genes controlling its phenotype are needed. Once the cell type has been identified, where required for the method an expression cDNA library is constructed of the cells as they are expressing the phenotype.

In general three methods are available for the gene inactivation step: Genetic Suppressor Element (GSE) [Holzmeyer et al, 1992; Roninson et al, 1995; Gudkov et al, 1994], Random Homozygous Knock-Out (RHKO) [Li and Cohen, 1996], and Technical Knock Out (TKO) described herein above. Of these methods the TKO method is preferred as it adaptable to the second step of the present method as described herein below in Example 1. Any method for gene inactivation may be used with existing or later derived methods which can be adapted to work with the second step of the present method is preferred.

Following gene inactivation treatment, an aliquot of the treated cells are exposed to a positive selection. That is, the cells are exposed to conditions requiring/activating the phenotype of interest. A reserved aliquot of the treated cells is not exposed. Following positive selection cells which continue to express the desired phenotype remain and those cells which cannot maintain the phenotype are lost. The method then provides for determining the gene that was not expressed in the lost cells by a "subtraction" analysis by any method known in the art, generally utilizing a comparison between the reserved cell aliquot and the cells remaining after positive selection. It should be noted that many aliquots can be tested and screened. The gene(s) identified is at least one of the genes which controls the phenotype.

The relative abundance of the differences between the "targeted" and "untargeted" aliquots are simultaneously compared using a "subtraction" analysis (differential analysis) technique such as differential display, representational difference analysis (RDA), GEM-Gene Expression Microarrays (Schena et al., 1995; Aiello et al., 1994; Shen et al., 1995; Bauer et al., 1993; Liang and Pardee, 1992; 1995, Liang et al., 1993; Braun et al., 1995, Hubank and Schatz, 1994; U.S. Pat. No. 5,545,531), suppressive subtraction hybridization (SSH) and direct sequencing (WO96/17957).

In the preferred method the procedure involves the transfection of targets cells with an anti-sense expression library followed by the positive selection of cells which have maintained a specific phenotype in the face of a specific challenge to the phenotype. It should be noted that one construct can be tested or many can be tested simultaneously in this method including over 100,000 constructs from an expression library. Cells in which an anti-sense inactivation has targeted a "sense" gene essential for the selected phenotype will be lost during the selection. Applicants have found that in general one cell has incorporated only one construct.

In this embodiment the next steps are to identify and isolate anti-sense expression vectors that are lost from the cell population due to cell loss during positive selection, that is, that induce a disadvantage in transfected cells during specific, positive selection resulting in the loss of the cell carrying the vector. These vectors are identified by subtracting the anti-sense expression vectors present after the selection from those present before the selection utilizing the reserved cell aliquot. This difference represents the vectors that express anti-sense against gene(s) that are essential for the maintenance of the selected phenotype.

These vectors are then recloned and sequenced. The identified anti-sense expression vectors are re-tested individually for the ability to inactivate the specific phenotype. With the sequence identified, the sense gene controlling the phenotype of interest can be identified using standard methods known in the art.

More specifically, the first part of the method consists of transfecting a target cell culture aliquot with an anti-sense expression library. The library is generated by cloning a cDNA library in the anti-sense orientation into an expression cassette that will express the anti-sense strand at a high efficiency. The cassette also contains a resistance marker that allows for selection of cells that have been successfully transfected. The cells that are transfected are ones that express a phenotype of interest.

The transfection results in a pool of cells that will express anti-sense messages against a large number of the genes expressed in the cell. These anti-sense messages will inactivate the functional expression of the corresponding sense message. This results in a pool of cells "knocked out" for the expression of many different genes. In many cases due to the vector system used, applicant have noted that the resulting cells will contain only a single anti-sense expressing vector.

When a transfected cell looses a specific phenotype, the anti-sense identity of the sense gene that has been knocked out is identified by isolating and sequencing the anti-sense expression cassette in the reserved unselected (untreated) aliquot. The anti-sense strand on the anti-sense expression cassette is the compliment of the sense gene. If the anti-sense strand in not a full length anti-sense, or does not match a sequence of a known gene, then the gene fragment can be used as a hybridization probe in order to isolate the full length gene. In essence, the anti-sense expression vector serves as a tag to identify the gene inactivation event of interest.

The method involves the selection of the pool of anti-sense expressing cells for the specific phenotype. The goal of the selection is to separate the majority of cells which continue to maintain a specific phenotype from the rare cells in which an anti-sense inactivation event has specifically knocked-out a gene that is essential for the maintenance of the specific phenotype.

This can be based on virtually any kind of positive selection means. These selection means can be varied as is known to those skilled in the art. However, the following is a non-exhaustive list and is not to be construed as limiting the present invention to these listed means.

The selection means is based on the ability of the cells to:

1. Grow or survive under specific culture conditions, that is the actual selection is for the growth or survival of the cells. In an embodiment, this can be basic culture conditions, such that the selection is for growth or survival-essential genes. The selection conditions could include sub-effective doses of specific factors which at effective doses would cause growth arrest or cell killing. In this case the selection is for the identification of knock-outs which sensitize the cells to the specific added factor.

In another embodiment, the selection can be in combination with a factor that normally does not cause an arrest or killing function. In this case a knock-out could be selected which only in combination with the added factor are effective in arresting or killing cells.

In a further embodiment, the selection can be for the inability to grow or survive when a parasite or infectious agent is added to the cell of interest. In this case the selection would be for knock-outs that are targeting genes that are specifically essential for some aspect of viral or parasitic function within a cell that are only essential when that cell is infected. Since some viral infection result in the induction of survival factors (such as CrmA, p35) it is likely that at least some cell functions are different and potentially selectively needed during viral, parasite growth.

2. The second type of selection means is for the expression of a specific factor that can be measured and this measurement can be adapted for a selection. This factor can be anything that is accessible to measurement, including but not limited to, secreted molecules, cell surface molecules, soluble and insoluble molecules, binding activities, activities that induce activities on other cells or induce other organic or inorganic chemical reactions.

3. The third type of selection means is for changes in cell structure that are detected by any means that could be adapted for a selection scheme. This includes, but is not limited to, morphological changes that are measured by physical methods such as differential sedimentation, differential light scattering, differential buoyant density, differential cell volume selected by sieving.

4. The fourth type of selection means is based on differences in gene expression that can be directly measured. This includes changes in cell surface markers, changes in biochemical activities, any changes that would be re-selected in changes in binding of fluorescent labeled probes that could be used in conjunction with a Fluorescence Activated Cell Sorter (FACS) or any property that can be used as a basis for a selection.

5. The fifth type of selection means is based on differences in gene expression that can be indirectly measured. This includes changes in transcription factor activity that are measured by a synthetic gene construct encoding a selective marker (such as a drug resistance marker or a cell surface marker that could be used in a FACS selection). This category would also include changes in mRNA stability, mRNA localization, mRNA translation control. All of these changes could be the basis of a selection because a synthetic construct which is controlled by one of these regulatory events could be constructed which would drive the expression of an easily selected gene product.

The third part of the method involves steps identifying the anti-sense knock-outs that specifically inhibit the phenotype of interest. Since the selection of the anti-sense transfected cells is based on the maintenance of the phenotype of interest, the cells of interest (those loosing the phenotype) will not be present after the selection but will be present before the selection. Since the functional changes are caused by expression from anti-sense expression vectors and the inactivated genes can be identified by sequence analysis of the cloned anti-sense cDNA insert, the goal of this step is actually to identify the anti-sense expression vectors that are lost from the population of cells during the selection procedure.

The anti-sense inserts are cloned into a defined position on the vector and the sequence elements surrounding the site are known, so all the cDNA inserts can be amplified with the use of a PCR amplification using primers from the sequences that surround the insert site. Thus the goal becomes to identify DNA molecules present in one population and not in another. This is accomplished by a variety of subtraction techniques. Some of the methods that will be used are summarized below as is known to those skilled in the art. However, the following is a non-exhaustive list and is not to be construed as limiting the present invention to these listed means. Various differential hybridization methods as well as different subtractive hybridization techniques will be used. They are summarized in some detail in the methods section.

Once fragments are identified that are lost during the selection and are candidates for genes of interest their function must be confirmed and the gene identified in the fourth part of the method. The fragments will be recloned into the anti-sense expression cassette and individually re-transfected into the target cell to determine whether the expression of the isolated fragment can really change phenotype. If the phenotype is really lost as is predicted then the isolated fragment will be sequenced and used to isolate the full length sense gene. It will also be determined whether the fragment is indeed anti-sense with the use of strand specific probes. The sense gene fragment will be used to derive antibodies that can be used to monitor expression levels to determine if there has been a functional anti-sense knock-out [Deiss et al., 1995].

The present invention is a genetic method for identifying genes that are essential for the maintenance of specific cell phenotypes. The method requires that the specific phenotype can be positively selected. These identified genes are excellent targets for the development of pharmacological inhibitors which would also act clinically to inhibit the specific phenotype. Thus the present invention provides a gene discovery tool which can effectively identify pharmacological targets for inhibition of deleterious phenotypes.

The following are several examples but this list is not to be construed as limiting the present invention to these listed examples.

Phenotypes Related to Growth or Survival

Addressing the problem of unusual growth: This includes the problem of cancer but is not limited to cancer but is applicable to all aberrant growth events. The method of the present invention can be used to identify genes that are essential for the growth of cells transformed under general or specific conditions.

To define genes that are essential specifically for transformed cells, an anti-sense cDNA library would be introduced into a transformed and the non-transformed cells that it was derived from. The anti-sense constructs that interfere with transformed cell growth and not from the non-transformed cells are found by subtracting the anti-sense RNA molecules expressed in surviving cells from both transfections. Knock-outs specifically absent in the transformed cells but present in the non-transformed cells are desired. These are isolated by the methods described herein. The selection can be a most specific selection such as one where sub- lethal doses of chemotherapeutics are added during the selection. In this case the selection would include gene knock-outs that sensitize the cells to chemotherapeutic treatments.

The factors added during the selection could be ones that are thought to be present at the site of tumors. Thus the selection would include events that sensitize cells to a localized tumor effect and could increase the specificity of anti-cancer treatment. Any growth or survival event could be used as a basis not just cancer related.

The growth or survival phenotype can also be used as a way of eliminating populations of cells that are not necessarily growing improperly but which function in a manner that is deleterious. Thus virally infected cells or parasite harboring cells could be used as a target and the un-infected or non-parasite containing cells used to subtract. This would define all the genes that are specifically essential for the cell in the presence of these insults. These would of course be excellent targets for inhibiting viral or parasite spread.

Phenotypes Related to the Release of Factors

This class of selections includes events that increase or decrease the production of secreted factors. These include inflammatory mediators whose release could be modulated. For example, if the production of a specific mediator is necessary for normal immune function but is produced at lethal levels in aberrant situations (such as septic shock), then one could use the production as a screen and look for events that knock-out or down-regulate productions. In a further embodiment, the selection can be done in the presence of sub-optimal doses of other drugs in order to identify sensitization events.

Phenotypes Related to Changes in Cell Functions

These selection events are designed to identify genes that are essential for many basic cell functions that depend on any changes that can be externally selected.

Figure 2:
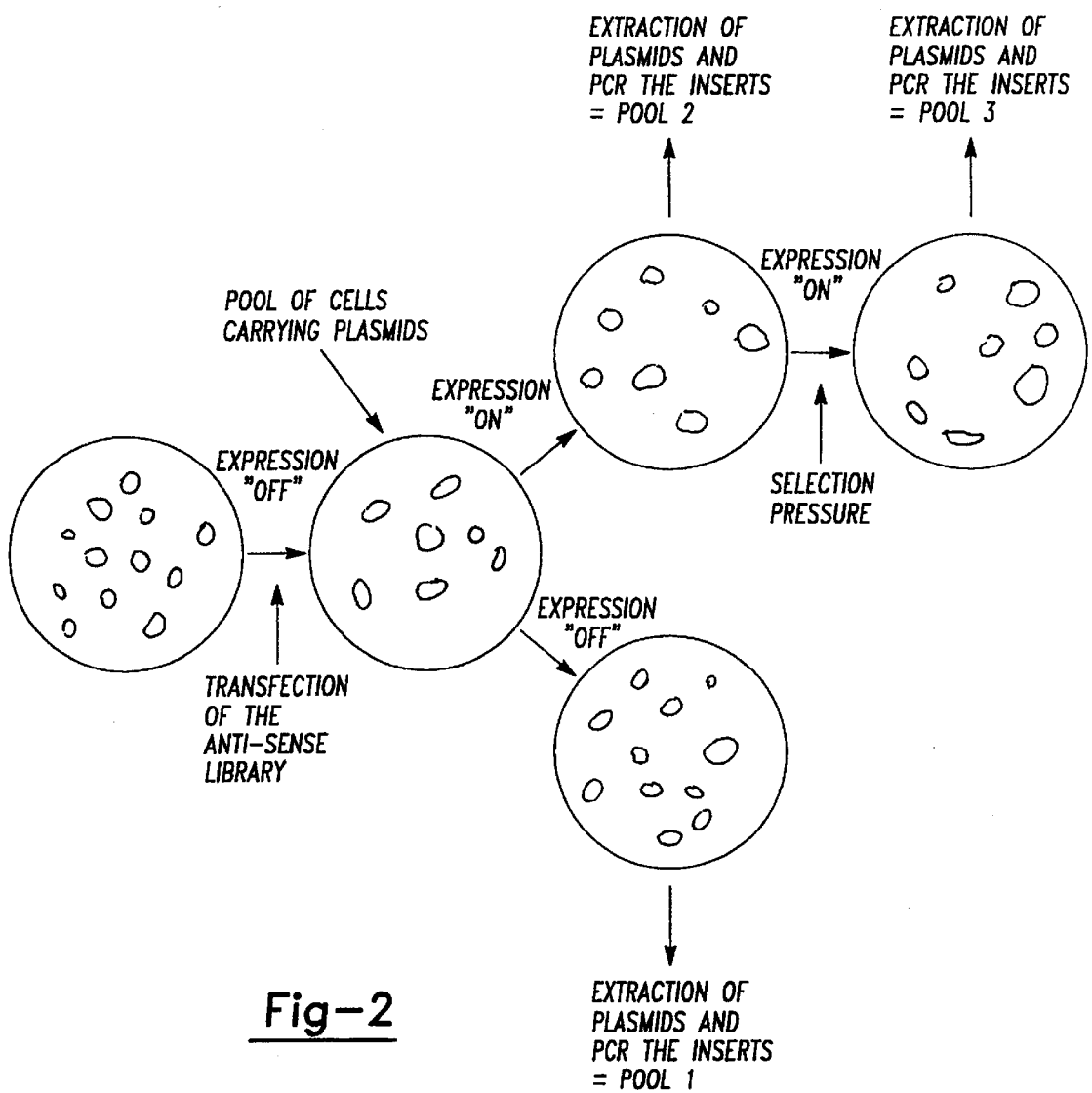
FIG. 2 is a schematic representation of the method of the present invention with a regulated anti-sense cDNA expression library.

Several permutations of the method of the present invention are possible and are presented as schematic diagrams in FIGS. 1–2. FIG. 1 provides a general outline of the gene identification method of the present invention. In this version a population of cells is first transfected with an antisense cDNA expression library. The expression library in this scheme codes for a drug resistance marker that is used to select transfected cells. This results in a population of cells (Population 1) that all contain anti-sense expression cassettes. The population of transfected cells is then placed under a selection pressure. Cells that survive this selection constitute population 2.

Transfected cells that become sensitive to the selection procedure will be lost or at least reduced in abundance in population 2. In order to identify the constructs that induce this sensitization the following procedure is performed. The expression cassettes contained in the two population are extracted from the cells. The cDNA inserts are excised by PCR amplification using primers that flank the cDNA cloning sites. This results in two pools of PCR fragments. To identify the elements that are lost during the selection a subtraction is done between the two pools. Elements are identified that are present in population 1 and absent or reduced in abundance in population 2.

To confirm that the subtracted fragments do indeed induce a sensitization to the selection procedure, individual fragments are recloned into the identical vector and than individually retransfected into cells. These cells are then individually assayed for sensitivity to the selection procedure. A correctly cloned element will induce sensitization of the transfected clones to the selection procedure.

FIG. 2 provides a diagram of the method with a regulated anti-sense cDNA expression library. In this simple variation the object is to clone the anti-sense cDNA library into a vector in which expression of the anti-sense is regulatable. The method is then modified so that during the original transfection, the expression of anti-sense is turned "OFF". After cells are selected for the presence of the vector an aliquot of cells is harvested and vectors are extracted and inserts excised by PCR. This constitutes pool 1. The remaining transfected cells are treated to turn "ON" the expression of the anti-sense expression. An aliquot of these cells are taken after several cell divisions (pool 2). Again the aliquot of cells are extracted and cDNA inserts excised by PCR. Finally an aliquot of the cells with anti-sense turned "ON" is placed under a specific selection and cells after this selection are harvested. Again following extraction and PCR amplification we have pool 3.

In this case we can perform two kinds of subtractions. The first subtraction would be pool 2 from pool 1. This identifies anti-sense inactivations that are lethal or growth arresting. The second subtraction, would be subtracting pool 3 from pool 2. This will identify anti-sense knock-outs which sensitize cells to the specific selection.

Additional permutations/variations on the method of the present invention can be made. The method can be used to identify different gene expression backgrounds. In this variation anti-sense induced sensitization in cells that express different genes is investigated. This can be accomplished by transfecting into cells that contain an inducible gene expression cassette. This cassette affords inducible expression of a specific gene construct we will call gene X for this example. Following transfection and selection for the presence of an anti-sense cDNA library and aliquot of cells is harvested, vector extracted and cDNA inserts excised by PCR. This is pool 1. The remaining cells are induced to express gene X. Allowing some time for expression, the cells are harvested, vectors extracted and cDNA inserts excised by PCR. This generates pool 2. The subtraction of pool 2 from pool 1 yields inserts that specifically sensitize cells to the expression of gene X.

In another variation the method of the present invention is used with different cell types. This variation involves transfecting two different cell types. This could be cells of different genetic background or of different tissue origins, or even from different organisms. In the simple diagramed case two cell types are transfected with the same anti-sense cDNA expression library. The different cell types are propagated in different containers. Transfected cells are then selected for the presence of the library. The cells containing the library are harvested, vectors extracted and cDNA inserts are excised by PCR. For each cell type a different pool is generated. The subtraction between these pools, both pool 1 from 2 and pool 2 from 1 identify anti sense knockouts that are specifically lethal or growth arresting to one cell type but not the other.

In a further variation, the method of the present invention is used for determining the fitness of specific genes in a population. In all the versions described above, populations of PCR fragments are generated which potentially differ by some number of elements due to the biological activity of those elements. The subtraction of these pools is then used as a method to identify cDNA fragments which have biological effects when expressed. It is also possible to use the same pools to determine whether an anti-sense construct directed against a specific gene could confer some biological effect during some sort of selection. Specifically in this simple example, when two pools 1 and 2 have been generated for the operation such as in the examples, there are a variety of tools available to individually measure the relative abundance of anti sense construct representing specific cDNAs in pool 1 and pool 2. A variety of methods are known for quantitating the abundance of DNA molecules in different samples. Following is a non-exhaustive list: Southern blot analysis either using a fragment of the gene of interest as a probe against the two pools; Quantitative PCR with specific primers identifying the gene of interest; GEM analysis, using the pools 1 and 2 as the probes and hybridizing against chips of arrayed known genes. If the abundance of the anti-sense construct significantly decreases after a selection then it is likely that anti-sense has sensitized the cells to that selection.

As shown in Example 2 and Table 2 herein below, sequences of genes have been identified by the method of the present invention (SEQ ID Nos:15–36). An antisense construct of these sequences delivered to a cell reduces a gene product (gene inactivation) and thereby provides sensitization of the cells to anti-Fas antibodies. In a preferred embodiment the sequences are SEQ ID Nos:19,20,23,25,26, 36. These antisense constructs can be used therapeutically to sensitize the cells for antibody therapy. Antisense therapeutic construct can be delivered to the cells and can be rendered nuclease resistant as is known in the art [Agrawal, 1996; Calabretta, et al, 1996; Crooke, 1995; Felgner, 1997; Gewirtz, 1993; Hanania, et al 1995; Lefebvre-d'Hellencourt et al, 1995; Lev-Lehman et al., 1997; Loke et al, 1989; Wagner et al., 1996; Wagner, 1994; Radhakrishnan et al., 1990.]

The present invention also discloses novel gene sequences as set forth in SEQ ID Nos:18,21,25 and 30–32.

The present invention also provides for a customized kit to practice the method of the present invention. The kit would be assembled to include at least an expression cDNA library constructed for specified cells as they are expressing the phenotype. Further a culture of cells of the requested phenotype could also be provided in the kit.

The above discussion provides a factual basis for the method of identifying genes that are essential for the maintenance of specific cell phenotypes. The methods used are shown below and can be shown by the following non-limiting examples and accompanying figures.

EXAMPLES

General Methods

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989).

Polymerase chain reaction (PCR) was carried out generally as in PCR Protocols: *A Guide To Methods And Applications*, Academic Press, San Diego, Calif. (1990). Reactions and manipulations involving other nucleic acid techniques, unless stated otherwise, were performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference.

Recombinant Protein Purification is undertaken as generally set forth in Marshak et al, "Strategies for Protein Purification and Characterization. A laboratory course manual." CSHL Press, 1996 unless otherwise specified.

Vectors are constructed containing the cDNA of the present invention by those skilled in the art and should contain all expression elements necessary to achieve the desired transcription of the sequences (see below in specific methods for a more detailed description). Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors are introduced into cells or tissues by any one of a variety of known methods within the art (calcium phosphate transfection; electroporation; lipofection; protoplast fusion; polybrene transfection). The host cell can be any eucaryotic and procaryotic cells, which can be transformed with the vector and which will support the production of the enzyme. Methods for transformation can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa, et al. (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

General methods in immunology: Standard methods in immunology known in the art and not specifically described were generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays: In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, New York, 1989.

Polyclonal and Monoclonal Antibody Production

Antibody Production: Antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W. H. Freeman and Co., 1992.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies the technique involves hyperimmunization of an appropriate donor with the protein or peptide fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W. H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

Specific Methods

Construction of Anti-sense Expression Vector

This method is not limited to any specific vector system. The actual requirements are that the vector system express at high levels anti-sense molecules and that they can be identified. In a preferred embodiment the Epstein Barr Virus (EBV) Episomal vector is used [Deiss et al, 1991].

The EBV episomal vector consists of DNA segments that are necessary for the episomal maintenance of the episome both in bacteria (E. coli) and in human cells (this include an origin of replication and a trans-acting factor (EBNA-1). The episome also includes genes encoding resistance markers for selection either in bacteria or in human cells. Finally the vector contains a transcription cassette. Initially it will be based on the vector as described in Deiss et al. [1991], but the present invention contemplates any transcription cassette that produces high levels of anti-sense expression. The EBV episomal vector contains a RNA Polymerase II promoter and or enhancer driving the transcription of a synthetic transcript containing a set of cloning sites, a splice donor and acceptor site and a polyadenylation signal, followed by a second set of enhancers. This vector can be efficiently shuttled from animal cells to bacteria and vice versa. One procedure that allows for rapid shuttling is using the method of Hirt [1967] to extract episomal vectors from animal cells and using this preparation to transform E.coli. Applicants have observed that, on average, cells transfected with a library cloned into the vector contain only one expressing vector.

The specific choice of promoters and enhancers are dependent on the exact selection condition and the cell line used. This must be empirically determined for each selection condition as is known to those skilled in the art.

In an embodiment, the EBV vector can also contain an inducible expressed promoter such that the expression of the anti-sense library would be inducibly expressed by a specific inducer. This will allow additional flexibility in designing selection protocols.

Construction of Anti-sense cDNA Library

There are several methods available to construct directional cDNA libraries. Any of these methods would be sufficient since they result in the production of a directionally identified cDNA library and the practitioner can use the method they are most familiar with. The directional cDNA is then cloned into the expression cassette in the anti-sense orientation. A method that may be used is detailed in Deiss et al, 1991. Briefly, it consists of making cDNA by the method of Gubler and Hoffman [1983] and making the cDNA directional by the method of Meisner et al. [1987].

The mRNA is extracted from cells that have been cultured under a variety of conditions that mimic the actual selection conditions. This is designed to ensure that the library will include all the messages that are expressed in the target cell under selection conditions. RNA is prepared at time points that would contain messages that are always present as well as messages that are induced by the selection procedure. This is achieved by extracting RNA previous to the selection and at times during the selection. The various pools of RNA are then mixed together so that all possible RNA molecules are present [Deiss and Kimchi, 1991].

An alternative method that can be used consists of deriving a library of genomic DNA fragments cloned into the expression cassette. Since all the transcribed messages are derived from genomic DNA (with the exception of RNA edited messages; this will actually include mitochondrial DNA as well) this method would generate all possible messages. The directionality would be lost so the library would be only half anti-sense. Since the sense fragments are unlikely to frequently encode full length proteins or have biological activity the anti-sense fragments would still likely produce the most frequent biological effects. The genomic fragments are produced by restriction enzyme cleavage of genomic DNA. Only one library per species would be necessary to produce, since with the exception of the B and T cell receptors, genomic DNA does not differ in different cell types at least in mammals (again erythrocytes or any cells that lack nuclei are an exception).

In the case of the genomic library it will be necessary to determine whether any expressed fragments express a sense or an anti-sense message. This is done by using the insert as a strand specific probe both from the expressed and non-expressed strand in a Northern analysis. This indicates if the expressed fragment is sense or anti-sense in relation to the endogenously expressed gene.

Some sequence will match, some will not match, genes already deposited in the various databases. In the case where the identified gene matches the sequence of a gene already in a database this information would then enable the determination if the insert is a sense or anti-sense insert.

Transfection of the Anti-sense Library

There are a large variety of methods to transfect DNA into cell lines and cell cultures. The most efficient method for each selection will be determined empirically based on experience and the known relative efficiency of each method.

The method selected must both efficiently delivery DNA into cells and not effect the biological responses that will be selected following the transfection. Viral vector system can also be used and this would entail producing infectious virus and infecting the target cells. Applicant has found electroporation to be an efficient method, but other methods can be used as are known in the art.

Identification of Differentially Expressed Antisense Messages

The methods of identifying the differentially expressed antisense messages in a preferred embodiment will include the methods described in Braun [1996] and as described in Diatchenko et al.[1996]. These methods include a PCR amplification of subtracted populations. Appropriate restriction sites are included in the expression vector so that following PCR amplification of the cDNA inserts, the inserts are flanked by appropriate restriction sites. Restriction digestion is then used to produce templates that are useful for these techniques.

Another method that is used is the "GEM" gene expression microarray as described in Schena et al. [1995]. In this technique, PCR fragments corresponding to a set of specific plasmids (in this case antisense cDNA inserts contained in antisense expressing vectors or other DNAs as appropriate) are fixed to a glass template and this is hybridized with two fluorescently labeled probes. In this specific case, the probes are reverse transcribed antisense transcripts derived from cells transfected with the antisense expression library either before or following a selection.

Generation of Efficient Antisense Inhibitor

In addition to assaying expression cassettes where all the transcripts are directionally cloned in the antisense orientation, another strategy employed in the present invention is to generate randomly primed cDNA and cleave the cDNA with two restriction enzymes X and Y and clone the resulting mixture into two different expression cassette. In the first cassette site, X, would transcriptionally precede Y and the second cassette site, Y, would transcriptionally precede X. In this arrangement, the cDNA is divided into sections that may have different abilities to serve as an efficient antisense inhibitor. The strongest differential signal is likely to be produced by the fragment that is the most efficient antisense inhibitor. Thus, the screening is more likely to produce a meaningful differential signal.

Specific Examples

Determination of Combination of Methods for Preferred Embodiment

The method requires two distinct major steps as described herein above. It is greatly advantageous if this method can be applied to a wide variety of cells. It is therefore useful if both steps could be applied to a wide variety of situations.

In the first step genes are inactivated in order to determine whether individual genes are essential for a specific phenotypic change. It is advantageous if these inactivation will have a phenotype both in haploid cells and in diploid cells. Since many cells of interest are diploid in nature. Furthermore, it is also an advantage if the inactivation method allows for the rapid identification of the inactivated genes. This can be achieved in a variety of manners. The inactivation methods are generally based on one of three different principles.

The first principle is that genes can be functionally inactivated by expressing mRNA that is derived from the anti-sense strand of the sense message. This allows for inactivating the mRNA in the cell and does not require a specific gene dose. This can work for single copy or multiple copy genes either from haploid or diploid organism. It has been shown that anti-sense inactivation can be effective in a wide range of organisms including bacterial, plant and animal. Applicants and others have extended the original observation by generating anti-sense expressing cDNA libraries. Applicants termed this method Technical Knock Out (TKO). These libraries contain collections of many (usually 100,000 to 1,000,000) different anti-sense expression constructs that will individually express a single anti-sense RNA molecule when transfected into appropriate target cells. Since these libraries contain large collections of these vectors they in effect can express anti-sense RNA to virtually all expressed mRNA molecules. Several investigators have used these type of libraries to inactivate genes and change the phenotype of cells. Once an altered cell is identified the expression cassette contained in the cells can be identified since the expression cassette DNA sequence is known. Subsequently, the anti-sense expressed cDNA molecule that is contained in the expression cassette is identified. This can be achieved by a variety of methods; applicants have used two methods. The first method involves shuttling the vector from animal cells into bacterial cells. Once the vector is in bacterial cells it is easy to produce large amounts of the vector for further analysis. The second method we have employed involves PCR amplification of the cDNA inserts by designing PCR primers that flank the cDNA cloning site on the vector. The flanking vector sequences are known so it is easy to chose appropriate primers. PCR amplification with these primers amplifies any cDNA molecules that were present between the two primers. The anti-sense approach also allows for tagging of the inactivation event. That is the identity of the sense message generally can be determined by sequencing the anti sense construct. This construct can then be identified and isolated from the phenotypically altered cells.

The second gene inactivation method that fits these requirement is an inactivation method that relies on production of "dominant negative" fragments of genes from an expression cDNA library. This method is called the Genetic Suppressor Element method (GSE). It is based on the observation that small fragments of a gene when expressed may interfere with the normal function of the full length gene product and in fact interfere with the normal function. In this manner these gene fragments were called "dominant negatives". A GSE library thus consists of fragmented cDNA molecules which are cloned into an expression cassette. When expressed from translation initiation signals in the cDNA molecule or from translation initiation signals present in the expression cassette these gene fragments can interfere with gene function. In addition the libraries used in the GSE method also include some anti-sense fragments and therefore gene inactivation can occur either by anti-sense or by dominant negative inactivation of gene function.

The third method of gene inactivation that could be used is called "Random Homozygous Knock-Out (RHKO)". In this method gene inactivation is achieved in two steps. A retroviral vector is used to infect target cells. The integration of the retroviral element itself can lead to inactivation of one copy of a gene if the integration event itself functionally disrupts the normal transcription or activity of the gene in which it integrates. The retroviral vector used has an additional property that it encodes a transcription element that should transcribe into the chromosomal location in which it has integrated. In the case that this generates and anti-sense RNA transcript, additional copies of the gene could be inactivated. Thus this method also relies on anti-sense inactivation.

The TKO method was chosen for generating inactivations in these examples as the preferred embodiment because the other methods described above are not as compatible with the second step in the method of the present invention as the TKO procedure. However, as improvements become available in these methods they could be used.

In the GSE method both sense and anti-sense gene fragments are generated which are expected to have different biological activities. It is difficult to distinguish closely related gene fragments of this sort by the methods that will be used in the second part of the gene identification method of the present invention. Thus the rare molecules that cause biological changes when expressed would be very difficult to distinguish from many similar molecules that would not have biological effects. The molecules that do not have effects would in essence mask the active molecules.

The RHKO method was also difficult to adapt to a high throughput subtractive procedure. The potential anti-sense fragments generated in this procedure must be cloned out individually and this is a process that is hard to adapt to subtraction.

The TKO method was easily adapted to subtraction. The cDNA inserts contained in expression vectors should be all or at least mostly anti-sense in nature. The cloning procedure outlined in Deiss and Kimchi was used. This generates anti-sense cDNA libraries and results in libraries that are biased to be anti-sense. It is possible to obtain some sense cDNA inserts with this method. Thus since most of the fragments are antisense the subtraction step will be mainly between different cDNA fragments that were expressed as anti-sense constructs. Again the principle of the present invention is that the abundance of an anti-sense construct(s) that induces a disadvantageous phenotype will be reduced after a biological selection. We wish to identify these constructs. Thus the TKO method was the method of choice for the gene inactivation step of the present invention. It can be used in a variety of cell populations, both in haploid, diploid and aneuploid cells. It can be easily scaled up to involve 100,000 events or more without undue expense. And it can be easily adapted to the subtractive methods that are needed in the second part of the method of the present invention.

The second step in the gene identification method requires that we can identify the loss of specific anti-sense gene constructs from a large population of anti-sense constructs that are not lost. This can be accomplished in a variety of different ways. Because it is a great advantage to be able to identify specific losses in the presence of large numbers of molecules that are not lost we needed a method that has a high throughput capacity. One method that fits this requirement involves using high density arrayed chips such as the GEM chips. These are arrayed dots containing specific DNA molecules corresponding to genes. The dots are arrayed at high density on a glass coverslip with the position of each dot and the identity of the DNA molecule fixed on each dot precisely determined. Two probes derived from different population of DNA or RNA molecules are labeled with two different fluorescent dyes and hybridized to the arrays. After appropriate washing the relative binding of the dyes at each dot is determined. The amount of dye bound at each spot reflects the abundance of the gene fixed on that dot relative in the whole population. Thus when two populations of DNA molecules are labeled with different dyes one can accurately determine whether there has been a change in relative abundance of individual molecules in the population. If there is no change the ratio of the two dyes will be one. If there has been a change in abundance then the ratio of the two different dyes will also change. This method can rapidly measure the changes of large numbers of genes in a large population. A copy of the DNA fix on each dot is stored and can be retrieved for further analysis. Although in the following example we did not use the GEM method to measure the loess of anti-sense constructs it is a method that can be used in the practice of the present invention.

A second method uses to identify the loss of specific anti-sense gene constructs from a large population of anti-sense constructs that are not lost is called "Subtraction". This involves manipulating two populations of DNA or RNA molecules so that only molecules that are present in one population and not in another are recovered. The version that we actually used is called PCR-Select which is a commercially available kit from CLONTECH. Briefly 1. Two populations of double stranded DNA are generated. It is assumed that some of the dsDNA molecules are present in only one of the populations (or at least much more abundant in one population).

2. These populations are separately processed. The population that is assumed to have extra species of molecules is called the tester sample. The second population that is assumed not to have these specific species is called the driver. The tester population is separately ligated to two different linkers. This generates tester population 1 and tester population 2. The driver is left without linkers.

3. A series of manipulations including denaturation and renaturation of the driver and tester in various combinations is used. This results in generating a series of DNA molecules that have different set of linkers at their ends. The only product that can be effectively PCR amplified at the end of the manipulations are those that are present in the tester and absent (or reduced) in the driver. These molecules are easily isolated after the last PCR step.

The net result of this method is that a population of gene fragments that are present in one population and lost or absent in another population is rapidly isolated. This is exactly what is needed in the gene identification method. These PCR products can be isolated by standard techniques and be used for further analysis as shown in Example 2.

EXAMPLE 2

Identification of Genes in HeLa Cells that are Involved in fas Antibody Sensitivity The method of the present invention was applied to HeLa cells treated with anti-Fas antibody in order to identify genes that when knocked-out cause sensitization of HeLa cells to the action of anti-Fas antibodies.

HeLa cells are derived from a human cervical carcinoma and were used in the original TKO [Deiss and Kimchi, 1991]. HeLA cells were used as an exemplar of the method of the present system as they are easily grown in culture, are easily transfected and respond to anti-Fas antibody treatment.

Anti-Fas antibody (Kamiya Biomedical Company, Seattle, Wash., catalog number: MC-060) is directed against Fas/CD95/Apo-1, a transmembrane receptor that is known to signal a death response in a variety of cell types. This antibody is an activating antibody, that is, the binding of the antibody mimics the effects of binding of ligand. Applying the appropriate dose to responding cells has been shown to lead to induction of cells death (Deiss et al., 1996). HeLa cells respond to this treatment.

In this exemplar genes are identified that regulate the sensitivity of HeLa cells to killing by anti-Fas antibody. Specifically, genes are identified whose loss sensitizes HeLa cells to anti-Fas treatment.

The outline of the procedure is as follows:

1. HeLa cells were transfected with an anti-sense cDNA library.

2. Cells containing anti-sense expression vectors were isolated by selection with Hygromycin. Since the vector contains the Hygromycin resistance marker, the selection of the transfected cultures with Hygromycin generated a population of cells which contain the anti-sense expression cassettes.

3. Aliquots of this pool of cells were treated with anti-Fas antibody under two different experimental conditions. It should be noted that more conditions could be screened at the same time.

a. Treatment with a sub-lethal dose of anti-Fas antibody (10 ng/ml). Cells that are super-sensitive to treatment with anti-Fas antibody were killed whereas the majority of the population which is resistant to the treatment proliferated.

b. In the second condition, the cells were treated with a lethal dose of anti-Fas antibody (100 ng/ml). The cells were harvested at 24 hours, before the majority of cells had been killed. In this case, applicants were looking for anti-sense events that accelerate the killing associated with anti-Fas treatment as another type of sensitization.

4. Aliquots of the cells just before the treatment with anti-Fas antibody and just after the treatment with anti-Fas antibody were harvested. The DNA contained in each cell population was extracted.

5. The anti-sense cDNA inserts contained in these DNA samples were preferentially amplified through the use of PCR (see details below).

6. The pools of anti-sense cDNA fragments that were derived from cells after treatment were subtracted from those before treatment(see details below). This generated a set of cDNA fragments that were present in cells before treatment but were absent after treatment. These fragments are good candidates for sensitizing cDNA fragments. In other words, it is likely that expression of some of these fragments leads to the inactivation of genes which causes cells to become super-sensitive to anti-Fas antibody treatment. These super-sensitive cells are quickly killed at a lower dose of anti-Fas antibody or more rapidly than the majority of cells. These cells are therefore lost from the treated cultures but are present in the untreated population. Likewise, the plasmids inducing this super-sensitivity are present in the cells before treatment but are absent from the cell sample taken after treatment. Thus, these fragments are identified during the subtraction.

7. The cDNA fragments generated by the subtraction were cloned into the original expression vector. Appropriate restriction enzyme sites were generated or maintained during the subtraction procedure so that the recloned construct is exactly identical to the construct in the originally transfected cells. The sequence of the isolated cDNA fragments was determined. 8. The anti-sense expression plasmids containing the cDNA inserts that were identified in the method of the present invention were individually re-transfected into HeLa cells and the transfectant cells were assayed for sensitivity to anti-Fas antibody treatment.

Specific Materials and Methods

HeLa cells were transfected with anti-sense cDNA library cloned in the episomal vector, anti-sense expression vector pTKO-1. This is the same library described in Deiss and Kimchi [1991]. One million cells plated in a 100 mm dish were transfected with 15 μg of DNA containing the anti-sense cDNA library, by using the Superfect reagent (Qiagen, Santa Clarita, Calif.) as suggested by the manufacturer. Two days following transfection, cells were treated with Hygromycin B (200 μg/ml) (Calbiochem-Novabiochem Corporation, La Jolla, Calif.). Following two weeks of selection, the population of cells was completely resistant to Hygromycin B.

These cells were plated in triplicate at a density of $2.5 \times 10^6$ cells per 150 mm dish in the absence of Hygromycin B. One plate was treated with anti-Fas antibody at 10 ng/ml (clone CHI-11 Kamiya Biomedical Company, Seattle, Wash.) for five days, the second plate was treated with 100 ng/ml of anti-as antibody for 24 hours and the third plate was UN-treated for 24 hours. Following the treatments, the cells were harvested by washing twice with ice cold PBS (NaCl 8 g/liter; KCl 0.2 g/liter; $Na^2HPO^4$ 1.44 g/liter; $KH^2PO^4$ 0.24 g/liter; final pH of solution adjusted to pH 7.4 with HCl) and concentrated by centrifugation (15,000×g for 15 seconds). DNA was extracted by using solutions P1, P2 and P3 from the Qiagen Plasmid Purification Kit (Qiagen, Santa Clarita, Calif.). The cell pellet was resuspended in 200 μl of solution P1 (50 mM Tris-HCl, pH 8.0; 10 mM EDTA; 100 μg/ml RNase A) then mixed with 200 μl of solution P2 (200 mM NaOH, 1% SDS) and incubated five minutes at room temperature. 200 μl of solution P3 (3.0M Potassium Acetate, pH 5.0) were added and incubated two minutes at room temperature, followed by a ten minute centrifugation at 15,000×g. The clear supernatant was mixed with an equal volume of isopropanol and centrifuged at 15,000×g for ten minutes. The precipitated DNA was resuspended in 100 μl of water and stored frozen until use.

For PCT amplification of the cDNA inserts contained in these DNA preparations, the following reaction was set in a total volume of 100 μl: 1 μl of the DNA, 200 μl of dATP, dGTP, dCTP, dTTP, 500 ng each of primers prLPD#64 (SEQ ID No:2) and prLPD#65 (SEQ ID No:3); 10 mM Tris-HCl pH 9.0; 0.1 Triton X-100; 1.0 mM MgCl and 1 unit of Taq DNA polymerase (Gibco/BRL, Gaithersburg, Md.). This reaction was incubated in a Thermocycler 2400 (Perkin-Elmer, Foster City, Calif.) according to the following protocol: First, the reaction was heated to 94° C. for five minutes, then was cycled 25 times using the following three temperatures: 58° C. for one minute, 72° C. for five minutes, 94° C. for one minute. After 25 cycles, the reaction was incubated at 72° C. for seven minutes. This resulted in amplification of the cDNA inserts. The prLPD#64 and prLPD#65 primers were design such that the end of the cDNA insert that is proximal to the promoter in the pTKO-1 vector is exactly flanked by a HindIII restriction site (this site is present in the vector) and the end of the cDNA that is distal to the promoter in pTKO-1 vector contains a BamHI restriction site. The BamHI site was created by altering a single base in the sequence immediately adjacent to the distal cDNA insert site (prLPD#65), by PCR. When the library was generated [Deiss and Kimchi, 1991], this site distal to the promoter was generated by the fusion of a BamHI restriction site (derived from the cDNA fragments) and a BglII site (derived from the vector). This fused site is resistant to cleavage by either enzymes, but a single base change restored the cleavage by BamHI. Thus, the amplified cDNA fragments are flanked by a HindIII restriction site on the promoter proximal side of the cDNA and by a BamHI site on the promoter distal side. This allows the exact re-cloning of the fragments into the pTKO-1 expression vector with exact conservation of sequence and orientation.

Following the PCR reaction, the mixture was cleaved with BamHI and HindIII (Gibco/BRL, Gaithersburg, Md.) as described by the manufacturer. The digestion products were purified using the Wizard PCR Prep Kit (Promega, Madison, Wis.). This generated cDNA inserts with HindIII and BamHI ends.

These nucleic acid fragments were subjected to subtraction using the PCR-Select Kit (Clontech, Palo Alto, Calif.) according to the instructions of the manufacturer with the following modifications. The driver was the PCR products derived from the untreated samples and two testers were used. The first tester was derived from cells treated with 10 ng/ml anti-Fas antibody and the second tester was derived from cells treated with 100 ng/ml of anti-Fas antibody. First modification: the subtraction is done between dsDNA pools so no cDNA synthesis is required. The fragments generated from the previous step were used directly in the subtraction. Thus, applicants began at Step IV F3 in the instructions (preparation of the adapter ligated tester cDNA). The second modification was the replacement of the blunt end ligation of adapter 1 and adapter 2R with cohesive end adapters. These cohesive end adapters were ligated to the BamHl and HindIII cleaved PCR fragments generated in the step above. The cohesive ligation is usually more efficient than blunt end ligation and since applicants use cDNA flanked by different restriction sites allowing the orientation of the fragments to be maintained when recloning the subtracted products. If the blunt end ligation is used, it would not allow distinguishing one end from the other and applicants would not be able to determine the relative orientation of the cDNA in the original expression cassette. Thus, adapter 1 was replaced by an equal mixture of primers prLPD#80 (SEQ ID No:4), prLPD#81 (SEQ ID No:5), prLPD#83 (SEQ ID no:7) and prLPD#84 (SEQ ID No:8). Adapter 2R was replaced by an equal mixture of prLDP#82 (SEQ ID No:6), prLPD#88

(SEQ ID No:12), prLPD#89 (SEQ ID No:13) and prLPD#90 (SEQ ID No:14). The other primers were of identical sequence as described in the kit. Thus, primer prLPD#85 (SEQ ID No:9) is the sequence of PCR primer 1, primer prLPD#86 (SEQ ID No:10) is the sequence of nested PCR primer 1 and primer prLPD#87 (SEQ ID No:11) is the sequence of nested PCR primer 2R. The manual supplied by the manufacturer with the kit was followed from the point of ligation of the adapters to the tester (Section IV F3 in the Manual). 0.3 μg of the tester was taken for adapter ligation. The initial hybridization included 0.9 μg of the driver and 0.03 μg of the adapted ligated tester. At the conclusion of the subtraction, a final PCR reaction is done using nested PCR primer 1 (prLPD#86) and nested PCR primer 2R (prLPD#87). This material contains the cDNA fragments that were present in the untreated sample but absent from the treated samples. The product of this PCR reaction were re-cloned into the anti-sense expression vector. (Primers used in this example are set forth in Table 1.)

Re-cloning of the subtracted fragments was accomplished by cleaving the subtracted population with BamHI and HindIII and purifying the cleaved products with the Wizard PCR Prep Kit (Promega Madison, Wis.). The cleaved products were then directly cloned into the pTKO1-DHFR vector between the HindIII and BglII sites. This replaced the DHFR sequences with the cDNA. This is precisely the procedure that was used to generate the anti-sense cDNA expression library. Thus, the fragments that were generated by the subtraction were exactly re-cloned into the original anti-sense expression vector that was used to transfect cells at the beginning of the procedure. The re-cloned constructs exactly duplicate the constructs that were present in the library. The re-cloned constructs were introduced into bacteria and DNA was extracted from the bacteria following conventional methods. These DNA preparations were used as a template for sequencing in order to determine the nucleotide sequence of the isolated cDNA inserts. Primer prLPD#51 (SEQ ID No:1) was used in Automated sequencing using Applied Biosystems 377XL. DNA sequencer with Perkin-Elmer Dye Terminated Sequencing Kits (Perkin-Elmer, Applied Biosystems Division, Foster City, Calif.). In addition, plasmids carrying the re-cloned inserts were transfected into HeLa cells to confirm their ability to induced super-sensitization to anti-Fas antibody treatment in HeLa cells.

HeLa cells were transfected with 15 μg of plasmids or control vectors as described for transfection of the original library. The cells were selected for two weeks for resistance to Hygromycin B treatment (200 μg/ml). This selects for cells which contain expression cassettes. One million cells were plated in a 100 mm dish and treated with anti-Fas antibody. Effects of anti-Fas antibody on the transfected cultures were quantified by MTT assays as described by the manufacturer (Sigma, St. Louis, Mo.)

Analysis of the Isolated DNA Sequences

The clones were sequenced using primer prLPD#51 which anneals close to the edge of the cDNA which is distal to the promoter in the antisense expression cassette. Thus, in the case that the sequence matches the sense strand of a known gene then the insert is in the antisense orientation. Sequences were compared to the combined nonredundant database and the dbest compiled at the NCB1 using the Blastn program with default parameters (Internet address: http://www.ncbi.nlm.nih.gov/cgi-bin/BLAST/nph-blast?Jform=0). The sequences determined by the method of the present invention are listed in Table 2.

Clone LPD#599 (SEQ ID No:15) shows no match against known gene sequences in the nonredundant database as of Nov. 9, 1997, but does match several EST sequences such as a 99% match against gene bank entry AA043612. Sequence analysis indicates that this fragment is oriented in the sense orientation in the antisense expression library. Applicants have noticed that although the library is designed to preferentially express the antisense strand, there are some sense gene fragments included in the library [Levy-Strumpf et al., 1997].

Clone LPD#601 (SEQ ID No:16) shows no match against known genes in the nonredundant database as of Nov. 7, 1997, but matches many genomic clone pieces and many EST entries as for example a 95% match to a portion of gene bank entry N20920.

Clone LPD#602 (SEQ ID No:17) shows no match against known genes in the nonredundant database as of Nov. 7, 1997. It does show some similarity to a large number of gene back entries such as gene bank entry Z68269. Many of these matches are in the 60–70% range and may indicate a repeated sequence.

Clone LPD#606 (SEQ ID No:18) shows no match against known genes in the nonredundant database as of Nov. 7, 1997. It does shown some matches against mouse EST in the 80% range (gene bank entry W71379, W29410 and AA409950) and a stretch of a good match against a human EST (gene bank W19764).

Clone LPD#607 (SEQ ID No:19) shows no match against known genes in the nonredundant database as of Nov. 7, 1997. This clone does show a very good match against three EST (gene bank entries, T08248, H42827 and T30569). The sequence analysis indicates that this fragment was transcribed in the antisense orientation in the original library. Thus, reduction (inactivation) of the gene product that is encoded by the full length message representing this clone leads to supersensitization of cells to the treatment with anti-Fas antibodies.

CloneS LPD#608 and LPD#618 (SEQ ID No:20, SEQ ID No:26) show no match against known genes in the combined nonredundant database as of Nov. 7, 1997. They do shown a match with a large number of EST entries (for example, gene bank entry, AA335297, H14907 and AA009451). The sequence analysis indicates that this fragment was transcribed in the antisense orientation in the original library. Thus, reduction of the gene product that is encoded by the full length message representing this clone leads to super-sensitization of cells to the treatment with anti-Fas antibodies.

Clone LPD#609 (SEQ ID No:21) shows no good match against know genes or EST in the combined nonredundant database as of Nov. 7, 1997.

Clone LPD#610 (SEQ ID No:22) shows no good match against known genes in the combined nonredundant database as of Nov. 7, 1997, but does show a good match against several EST entries including gene bank entries AA447349, H24439, R72995, H17221 and R24985. Sequence analysis indicates that this fragment was in the sense orientation in the original library.

Clone LPD611 (SEQ ID No:23) shows no good match against known genes in the combined nonredundant database as of Nov. 7, 1997, but does show good matches with a variety of EST (including gene bank entries R76164, R25241, N66591 and N66577). The sequence analysis indicates that this fragment was transcribed in the antisense orientation in the original library. Thus, reduction of the gene product that is encoded by the full length message representing this clone leads to supersensitization of cells to the treatment with anti-Fas antibodies.

Clone LPD#613 (SEQ ID No:24) shows no good match against known genes in the combined nonredundant database as of Nov. 7, 1997, but a portion of the sequence shows homology to a large number of sequences and likely contains a repetitive element.

Clone LPD#616 (SEQ ID No:25) shows an excellent match with human tryptophanyl-tRNA synthetase (see emb X67928 for example). The sequence analysis indicates that this fragment was transcribed in the antisense orientation in the original library. Thus, reduction of tryptophany-tRNA synthetase leads to supersensitization of cells to the treatment with anti-Fas antibodies.

Clone LPD#619 (SEQ ID No:27) shows no good match against known genes in the combined nonredundant database as of Nov. 7, 1997, but does show good matches with the sequence of a human retroviral element called pHE.1 (for example emb Z95333, emb Z84475, gb M85205).

Clone L7_10_1_LPD (SEQ ID No:28) shows no good match against known genes in the combined nonredundant database as of Nov. 7, 1997, but does show very good matches against several EST (for example, see gb T77711, gb T78724, gb AA324254). Sequence analysis indicates that the fragment inserted in the expression library was in the sense orientation.

Clone L_7_10_2 LPD (SEQ ID No:29) shows no good match against known genes in the combined nonredundant database as of Nov. 7, 1997, but does show good matches with several EST (for example, see gb R12242 and gb H84498). Sequence analysis indicates that the fragment inserted in the expression library was in the sense orientation.

Clone E7_100_11_LPD (SEQ ID No:30) shows no good match against known genes or EST in the combined nonredundant database as of Nov. 7, 1997.

Clone L7_10_8_BS (SEQ ID No:31) shows no good match against known genes or EST in the combined nonredundant database as of Nov. 7, 1997.

Clone L7_10$_{13}$ 3 (SEQ ID No:32) shows no good match against known genes or EST in the combined nonredundant database as of Nov. 7, 1997.

Clone E7_100_10 (SEQ ID No:33) shows a good match with mitochondrial DNA (see gb L00016).

Clone L7_100_4_BS and L7_100_5_BS (SEQ ID Nos:34–35) show no good match against known genes in the combined nonredundant database as of Nov. 7, 1997. They do show good matches against several EST entries (for example, see gb AA227149, gb N46661, dbj C76104). Sequences analysis indicates that this gene fragment was oriented in the sense orientation in the original expression cassette.

Clone E7_10_9 (SEQ ID No:36) shows no good match against known genes in the combined nonredundant database as of Nov. 7, 1997. It does show good matches against two EST entries (see gb R54192, gb H39863). The sequence analysis indicates that this fragment was transcribed in the antisense orientation in the original library. Thus, reduction of this protein leads to supersensitization of cells to the treatment with anti-Fas antibodies.

As described above, the isolated fragments were recloned and then reassayed for sensitivity to treatment with anti-Fas antibody (50 ng/ml for 72 hrs) using the MTT assay. These assays showed that expression of fragments LPD#599 (repeated in triplicate with two different transfectants) or LPD#606 (repeated in triplicate) resulted respectively in a 1.6 and 2.0 fold increase in sensitivity to anti-Fas antibody treatment whereas expression of CrmA (a protective protein) resulted in a 2.3 fold reduction in sensitivity. This demonstrates that the method of the present invention can be successfully used to identify genes based on a positively selected phenotype.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer"

(iii) HYPOTHETICAL: NO (iv) ANTI-SENSE: NO (xi) SEQUENCE DESCRIPTION: SEQ ID NO:1:

```
TCTGTAGGTA GTTTGTC                                                             17

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:2:

TGGAGGCCTA GGCTTTTGC                                                           19

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

GTAAGGTTCC TTCACAAGGA TCC                                                      23

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

CTAATACGAC TCACTATAGG GCTCGAGCGG CCGCCCGGGC AGGTA                              45

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:5:

CTAATACGAC TCACTATAGG GCTCGAGCGG CCGCCCGGGC AGGTG                              45

(2) INFORMATION FOR SEQ ID NO:6:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:6:
```

```
CTAATACGAC TCACTATAGG GCAGCGTGGT CGCGGCCGAG GTG           43
```

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:7:

```
AGCTTACCTG CCCGG                                          15
```

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:8:

```
GATCCACCTG CCCGG                                          15
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:9:

```
CTAATACGAC TCACTATAGG GC                                  22
```

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:10:

```
TCGAGCGGCC GCCCGGGCAG GT                                  22
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

-continued (xi) SEQUENCE DESCRIPTION: SEQ ID NO:11:

AGCGTGGTCG CGGCCGAGGT                                              20

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:12:

AGCTTACCTC GGCCG                                                   15

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:13:

GATCCACCTC GGCCG                                                   15

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:14:

CTAATACGAC TCACTATAGG GCAGCGTGGT CGCGGCCGAG GTA                     43

(2) INFORMATION FOR SEQ ID NO:15:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GATCCAAGCG AAAAAGGGAA TAAGAAGGGA GGAATGTAAC TAGGAGCAGC TCCCAACAGT    60

TTGCCTATGT ATTTGCCAGC ACCAAAATTT GTAGAGTAAG CCACTTACAT TTCCACTGCT   120

AGTATTAAGG AAAGACAGCA GTGGTGATTT TTATAAAGCG AGTATACATT TATTTTTATT   180

CTGATATGTG AATTTTTCTT TCACGAGTTA ATTAACTGGT AATTTGTAAA CAGTGGGAAG   240

AAGATTAGAA CAATTATGGA GGTACTGAAT TACACAAGGA GATTAAAATG AAATGAATCA   300

ATCTACCTAT CTTGTGGTTA GTTAATATTT ACCATGATGC ATACACTTGA GAAATGAGAA   360

ATGCCCAAAT TGTATAATGC ATTATCTTNN TTATTATTTA TTNNNGTAAA TAATTCTTGC   420

```
TNNACATTAN NCTNCAAGGN TAGCTNTATC TATACTTGNT AGCTANNTTC TTATACAAAG      480

CANGNTNCTT TTGAANATGA TTTACCNATT AANTANANNA GCTTAGGTGC CTNNTTTNAC      540

TCTGGNTNGT CATNTTGNTT NNCTTTTNNC NANATCATAT ATAATTTCCA NNGAATGTTG      600

ATNTNTNTCC TCANNTTNCA TTNTANCCNG NGCNTATCCT NTNNNNTGNT NGNNTATGTC      660

(2) INFORMATION FOR SEQ ID NO:16:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GATCCTGGTA TAATGTGATT GAATTATGAA GGCAAATTTC TCATGAATGG TTCAGCACCA       60

TCCCCTTGTA CCATCCTCAC AATAATGAGT AACTTCTCAT GAGATGTAGT CACTGAAATC      120

TCTATATCAC CTCCCCACTC TCCGTGTTTT CTCCTTGCCA TGTGAGACAA TTGATTCTTT      180

CTTTGCCTTC CATGATTATT GAAAGATTTC TGAGGCCTAG AAGCAGAAGC ACTGTGCTTA      240

GAACCATGAG CCAATTAAAC CTCTTTTTCA AAATAAATCA TACGGGAAAT GGCAAATGAG      300

GACTGGAGCG TTGCTATAAA GATACCTGGA AATGTGGAAG CAGCTTTGGA ACCAGGTAAT      360

GGACGGAGGT TGGAAGAGTT TGGAGGGCTC AAAAGAAGAC AGATGAGAAA ACTTTTGGAC      420

CATCTTAGAG TCTGGTTCAA TGGTTGTGAC AAAAATCCTG ACAGAAACAT GGACAGTGAA      480

GGCCAGGCTG AGGAGGTCTC AGAGAGAAAT AAGAAGCTTT TTGCAA                     526

(2) INFORMATION FOR SEQ ID NO:17:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AAACATTATG CACAGAGGAA TAAAATTAAG AATGACCACA GTCTTCTCTT CAGAAATTAT       60

GCAAGCCAGA ATAGAGTAGA GCAACATCTT TACAGTTCTT AAAGAAAAAA TATATCAACT      120

TAGAATTCTA TACCCAGCAA AAATATATTT CAAAAGAAG ACACAATACT TTTTCAGACA      180

GACAAAAGCC AAGAGAGTAA TTCCAGGGAC GTGTAATATA AGAAATATTA GTGAAAGTAG      240

TGTAAAGAAT GAGAGAGAGG AAATATAAGG ATACTGTTAT AATATCCCTA CACTGTACCT      300

TAAGTGGATT GTAATATTAT CTGAAGGTAA ACTGTAATAT GTTAAATAAA GATGTATATT      360

TTTAATCCTA GAGAAACTGC TATGAAAACA AAAGTAAAA CAAAGTGGTA TTACTAACAA      420

GCCAATAATG GAGATAAAAT GGGCAATAGA AAACAACAAC AAAAATTCAA TCCAAAAGAA      480

GGAAG                                                                 485

(2) INFORMATION FOR SEQ ID NO:18:

(i) SEQUENCE CHARACTERISTICS:
        (A) LENGTH: 183 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:18:

| | | | | | |
|---|---|---|---|---|---|
| GATCCCTCTG | GCACTGGGAT | GCTTCCACAG | ATGTACCTGA | AAAGTCGTCA | CTCTCTCACC | 60 |
| AAGGAGGAAG | AAGCAGTACT | TTTTTGTCTC | ATAGCATTAG | TAACCAAGCT | AATGTTCACC | 120 |
| AGTCTGTCAT | TAGCTCCTGG | CTCAGCACTG | ATCCTGCAAA | AGACCGAATT | GAAATCACAA | 180 |
| GCT | | | | | | 183 |

(2) INFORMATION FOR SEQ ID NO:19:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

| | | | | | |
|---|---|---|---|---|---|
| GGGACATGGT | TGGGCCATGC | CACACCAGGG | CTGGTGAGGC | AACCAGTTTT | GATTTTGACA | 60 |
| GAGTGGCTGG | AGGAAAAGTG | GCAATCAAGG | TGCTGCTTGG | TTTGCTCTGA | GTGCAAATGG | 120 |
| AACCAACAGG | TTTCTGCTGC | AATCTGTGTG | TTCCCAGTGC | CAGGTCACAC | CAGGAGGGGT | 180 |
| GGGGCAGGGC | TAACCAAGTG | GTCTCTGAAC | TCACCGAGCG | TCTGCACTTG | GTTGTGAAGT | 240 |
| TAATGGGAGT | ACAGAGAGCG | TCTGGCCTTG | GAGAGGGGTT | GAGAGCCTCC | TTTTTGGTTC | 300 |
| TTCATTCCTG | AGCTCTTGCC | TGCCCACAAA | TCTGACCTCT | TTGAATGGGG | ACGCAGTCCT | 360 |
| TCAACAGAGA | AGTTTCTATG | GCAAAGAAGT | TTCTATTTAG | CTCTAGATCC | AGCAGAGTCA | 420 |
| TCCATTCTAA | CTGCCCTGAA | GTCTAGAGCA | GGGGAGGGAA | CCCAGAGGCT | GGGGATGAGA | 480 |
| CTAGGCAGAC | CCTGGTTACC | ATATGGACAA | GGACAGGGGA | AAGCACCCCC | TTCCTCAATT | 540 |
| TCTGAAAGTT | CTATCTTTGG | GTTCGCTGGA | CTTTGAGGAT | GATAAAGAAC | ATNTAGGTAC | 600 |
| TA | | | | | | 602 |

(2) INFORMATION FOR SEQ ID NO:20:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

| | | | | | |
|---|---|---|---|---|---|
| AAGTGGGACT | CTGGGCCTCT | GACCAGCTGT | GCGGCATGGG | CTAAGTCACT | CTGCCCTTCG | 60 |
| GAGCCTCTGG | AAGCT | | | | | 75 |

(2) INFORMATION FOR SEQ ID NO:21:

(i) SEQUENCE CHARACTERISTICS:
        (A) LENGTH: 497 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

| | | | | | |
|---|---|---|---|---|---|
| GATCCTANAC | CTGCTCTTTC | TCTAATCTTC | TGTATCTTAG | CAATCGGCCA | AAAAACTTGA | 60 |

```
AATCATACTT GATTTCTCCT GGCCCTCAAA GCCTACATTC ATTCTGCCAA ATCATGTAAG      120

TCCATCTTTA AAATTTATAC TGACTGTGCA TTTCTTCTTA TCTCCATTAC TATCACCCAA      180

GTTCAAAATC CTTTCTTATT TTTCACCTGA GTATTGCAAT ATTTTCTTAG ATGACCCTAA      240

CTGATCTTGC CGTTTCTACT CTTGCTTTCC TACAGTCAAT TCTCTTCATA TATGCCAACA      300

TTACCTTTTA AAACTACAAA CAAGTTCAGG TTACTTCTTC CTTGCTCAAA GTCTCAAATA      360

TCTTTTTATC ACACACAAAT CAAAGGTGGC TAAGAATGGT CTGGGTCCTG CATACCTCTC      420

CAATGTCATC TACAGCATCT CTGACTTTCT CGCACTGCTC TGGTCACAGT GGTCTTCTTT      480

TTCTCTAATA CACTAAG                                                    497

(2) INFORMATION FOR SEQ ID NO:22:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TCCAGAGCAA ACATTACATC ATAGGCCATG GGGGTTGTCA CTTAGCTGCA TGCTAAGAAT       60

CCTCATATGC TGCTTTGAAA ACGCCATAAA AAACTAAGAT GCCCTCATAC ACAGAAAAAA      120

GGAGTTGGGC CAACAGCCTG CGAGAGAAGA TCCTTCCCAA CTCTGCCATT CTTACTGCAG      180

GAGGGTTTGT AATGCTTCCC CACTTCCTCA GGTCCAGCGA CTGCACCTCC ACCACTGGAG      240

TGGGGGACAC TTCCATTGCT GATGGAAGCT GCCTACTGCT TTTAAAAACA CACACATGAG      300

CTGAGAAGTT CTGCTGAAGG TGGGGAGAGT GCTGCTCTTG GCTGCCAGCC GGGTCTAGCG      360

GCCCTAACAA GGGAAACTGG CTGATACAAA ATGGATCACT GCCTGAGATA TATGAACTGG      420

ACTGAGGATA GAAGTTGCAT CCGCTGGGCA AAATGTGCCA AGAACAGAA AGTCTTTCAA       480

TTTATTCTTT TAGGCACCAA GAATAAATAA ATNCTAAGA                            519

(2) INFORMATION FOR SEQ ID NO:23:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GGGTGAAGCA TCTGNTTCAT NACACAGGGC TATCATAATT GGGTTCTGGA AATGGAATGG       60

GTCTCTAAAC ATTTTAATGC CCCAGCTTGG TATTGGACNC AATGCAAGAT GGCTAAAATC      120

TTCATTTAAA ATTCAAGGGT ATTGCTTGCT ATTTCACATT ATATACTTTT TAAATACTAT      180

TGCTCTTTGC ATATGAGGCA TTTCACTAAC CTTGGATCAT TGGATCTTAA ACATGATAAT      240

ATAGAATATC TGAACATTGG ACTTGNTCTT TAGAGTATAT GGCCTTTAGT TCTTGTGGAA      300

CTAAATACAG TGATTCTAAG ATCAAAAGTC TTAGTGTTTG GGGTTTTTTT TTCCTCTTTT      360

TGGATATGGG GTGTT                                                      375

(2) INFORMATION FOR SEQ ID NO:24:

(i) SEQUENCE CHARACTERISTICS:
        (A) LENGTH: 382 base pairs
```

(B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:24:

ATCCAGCGGN TCAGCACACA CTGGGGCCTA CCGGAGTGGG AGGGAGGGAC AGGGATGAGG      60

GAAAAATAAC TAATGGGTAC TAGGCTTAAT ACCTGGGTGG TGAAATAATC TGTACAACAA     120

ACTCCCATGA CACAAGTTTA CCTTTACAAA CCTGCACATG TACCCCTGAA CTTAAAGAAA     180

AGTTTTTTTA AAAAATCACA CTTCCAGAGT TTGCTAAATA ATTATGACCA GTATTTTACT     240

ACCATCTTCT TCCTTGGTGA ACTACTAAAA TTAGTAAATT TATGTTAAAA ATGAAGTTCT     300

CCCTAGAAAT CAAAAGTGCA GTCTAAGCAC TGAAAATGTT CTATCAACAC TTGTTAACTG     360

AGAACCATTG AAACATCTAG GA                                              382

(2) INFORMATION FOR SEQ ID NO:25:

(i) SEQUENCE CHARACTERISTICS:
            (A) LENGTH: 586 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:25:

TNCGGATGAG ATAGTGAAAG AGTTCATGAC TCCCCGGAAG CTGTCCTTCG GCTTTCAGTA      60

GCACTCGTTT TACATATGCT TATAAAAGAA GTGATGTATC AGTAATGTAT CAATAATCCC     120

AGCCCAGTCA AAGCACCGCC ACCTGTAGGC TTCTGTCTCA TGGTAATTAC TGGGCCTGGC     180

CCCTGTAAGC CTGTGTATGT TATCAATACT GTTTCTACCT GTGAGTTCCA TTATTTCTAT     240

CTCTTATGGG CAAAGCATTG TGGGTAATTG GTGCTGGCTA ACATTGCATG GTCCGGATAG     300

AGAAGTCCAG CTGTGAGTCT CTCCCCAAAG CAGCCCCACA GTGGAGCCTT TGGCTGGAAG     360

TCCATGGGCC ACCCTGTTCT TGTCCATGGA GGACTCCGAG GGTTCCAAGT ATACTCTTAA     420

GACCCACTCT GTTTAAAAAT ATATATTCTA TGTATGCGTA TATGGAATTG GAAATGTCAT     480

TATTGGAACC TAGAAANGGC TTTGGAATAT TGATGTGGGG AGGNTTATTG AGCACCAGAT     540

GTATTTTANC CCATGCCCCC TCCAAAAAGA AATGGTTAGT NAAAAC                    586

(2) INFORMATION FOR SEQ ID NO:26:

(i) SEQUENCE CHARACTERISTICS:
            (A) LENGTH: 84 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

GATCCTTNCA AGTGGGACTC TGGNCCTCTG ACCAGCTGTG CGGCATGGGC TAAGTCACTC      60

TGCCCTTCGG AGCCTCTGGA AGCT                                             84

(2) INFORMATION FOR SEQ ID NO:27:

(i) SEQUENCE CHARACTERISTICS:
            (A) LENGTH: 134 base pairs
            (B) TYPE: nucleic acid
            (C) STRANDEDNESS: single (D) TOPOLOGY: linear (ii) MOLECULE TYPE: cDNA (xi) SEQUENCE DESCRIPTION: SEQ ID NO:27:

CTNTGGANTA CANCNATCCC TGGATTTAAN GAGANGGCCA GGCCACTCTA TACTCTAATC      60

AAGGAGACCC AGAGGGCAAA TACTCATCTA GGAGAATGGG AACCAGAGGC AGAAACAGCC     120

TTCAAAACCT TAAA                                                      134

(2) INFORMATION FOR SEQ ID NO:28:

(i) SEQUENCE CHARACTERISTICS:
          (A) LENGTH: 332 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:28:

AATAAGGTTC CTTCACAAAN ATCCAAGCCA GCACCTTAGT TTTCCTACAA CATAAATGTA      60

ACAAAGTTAT CTTCTACTGT ATTGCACCTT AGTCCAAAAG TAAAACAACT AAATGAAAAT     120

TTAAATAAAT CAGACTGAAA AAGCCCAAAG AGTAAGAGGA ATACCTTATA AATGTGACTA     180

CCCACCTAAA AATTCTTGAA CTACTTTGTT TTGCATAGGA TTTTATGGGA CTAACCAAAT     240

GTTCCATGAA CCATGAGGTG AAAACTGCGA TTTCATGATA GCACATTGTT TTACAATTCT     300

GATTAGAAAT CCTTCAGAAA TATTTCTGTA TC                                   332

(2) INFORMATION FOR SEQ ID NO:29:

(i) SEQUENCE CHARACTERISTICS:
          (A) LENGTH: 311 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:29:

ANGTAAGGTT CCTTCACAAA AACCAAGCGG GACTCCNAAA CAACCATGGT GCAATGGTGG      60

CAAAAACTGG GGACTGGGTC TTTCTCGCAA CTTCTGTGCC TCCTTTCATT CTCAAAAAAG     120

GACTATTACC AAATGGGGGG GAAAAAACAT AAGCANAAAA AACCCCAAGG ACAAACTGGA     180

AATTTAATTC CTTNATGCAA ATCTTATCTT CATCTGGTGC CTCATTACCC TGGGCCCCAA     240

GCCTTCTAAT TAGGAAAAAA TACTGATTTC TGTTAGGCAA TTGCTTATNT TGGTGGCTTC     300

ATCACATTTC A                                                          311

(2) INFORMATION FOR SEQ ID NO:30:

(i) SEQUENCE CHARACTERISTICS:
          (A) LENGTH: 880 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:30:

CAAAGTACCA AGCCCGAGAA AATACAGGTC TATTCAATTC CACCTGCTAG CCTAAACTTC      60

AAGTAGACTT CAAAGCAATA CAAGTTTGTA TGGTCTTTTT GGCAATAGCA GGAAATGATA     120

```
CAAGCGAAAT CAGTTCTTGA TTAAGGGAGG AGCAGAATTG CATTAGTTAG ATATTCTGGT      180

AGTGCTGCAA ACTATAATGA TAAATGAAGG CAGCCCAAGA CTTAAGATGT AAAGTTATGT      240

AGCTCATGCA ATTCAATGTC AGTATTTGAA GGCTATATGA TGAATATTTC CAGAATTATA      300

ATGAAAAAAG TAAAAACAAA TTTGCCTCTT ACTGATGCTT CAAAAATCAT TTGTGTATAT      360

TTAACAAAAG AAGTGTCTAA ATAGATCTGA ATTTAAACCA CAGTACTGAA CACACTACAT      420

GAGGTAACAT TGAGTATTAT CAAAGTACCA AGCCCGAGAA ATACAGGTC TATTCAATTC       480

CACCTGCTAG CCTAAACTTC AAGTAGACTT CAAAGCAATA CAAGTTTGTA TGGTCTTTTT      540

GGCAATAGCA GGAAATGATA CAAGCGAAAT CAGTTCTTGA TTAAGGGAGG AGCAGAATTG      600

CATTAGTTAG ATATTCTGGT AGTGCTGCAA ACTATAATGA TAAATGAAGG CAGCCCAAGA      660

CTTAAGATGT AAAGTTATGT AGCTCATGCA ATTCAATGTC AGTATTTGAA GGCTATATGA      720

TGAATATTTC CAGAATTATA ATGAAAAAAG TAAAAACAAA TTTGCCTCTT ACTGATGCTT      780

CAAAAATCAT TTGTGTATAT TTAACAAAAG AAGTGTCTAA ATAGATCTGA ATTTAAACCA      840

CAGTACTGAA CACACTACAT GAGGTAACAT TGAGTATTAT                            880

(2) INFORMATION FOR SEQ ID NO:31:

(i) SEQUENCE CHARACTERISTICS:
        (A) LENGTH: 596 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

AAGCAAAAGG AATGCTTATA CACTGTTGGT AGGAGTATTA GGATTACAGG CGTGAGCCTC       60

CACTTCCAGC CGTCCACAAT CTATTGAGAT GACCATGTTC TTTTCTTCCT TCAGTCTGTT      120

GCACTAATCA TTTCCAGCTG ATGAAATAAC GTTGCATTCC AGGGATACAC TGTACTGGGT      180

ACTGGTGTAC ATTCCTGTTT ATATGTTACG GTATTTGGTT TGCCAAAATT TACTAGGAAA      240

TTTCACAGAT CCACTCATAA GCGATATTAT CAGAGTTTTC CCTGTGTATG ATGTTTCACT      300

TTGGTATCTA GATAACAATA GCATCATAGA ACCAGTAAAA AATATTACAT GCTCTTCCAA      360

GTTTTTAAGA CATTTTTATC GAATTGGTAA TTTTCATGTG TTTGGTATAA TATACAAAAG      420

AATACATTTG AACTGGGAAT TTACATGTGT GTCAGGGGCA GGGGTGAGAG TTTTTAAATT      480

ACCAATTTAT TGTCTTCACT TTGTTCTTGA ATGAGTTGTG GTAGTCAGTG TCTTTCTAGG      540

AATTTGTCTA CTTCCACAAA GATATTTGTC AAAATACTAA TCCCTTGTTA TGGGAA         596

(2) INFORMATION FOR SEQ ID NO:32:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

AAGCGGCACT CATCACTTCT ACCCTTATTT CTGCTGGCAG AAACCCAGTC ACAAGCTCCA       60

CTGACATGCA AGGAGATTTG GGAAATGCAG TCTCTGTCAG CTAGCCCAAA CTCTAAGAAG      120

CCAAAGGAAA TATGTATTTT GGGTGGAGAT CTAGCCATCT TACCACACTA TGGTGGTCCA      180

GTAGAGGTCT ATCAAAATAT TAATTCACAG AAGACTAAAG ACACATTTAC AATGAAGGTT      240
```

```
TACAAAACTT ATCTGCAAAG AAAAAGCCAG AACATGTTTT ATTGTGGAAT AGTTCTAAAA      300

TTGCTTATAG ATGAAAAGAA CAAAACAAAT ATTTAAATCA GTCACCTCTA GAATAGTGAA      360

AGGCCAAAAA CTGCATTTCA GAAATGAAAT ATCACTCTGG GA                        402

(2) INFORMATION FOR SEQ ID NO:33:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

AAGCGAAAAC ACCCTCATGT GAATGAGGGT TTTATGTTGT TAATGTGGTG GGTGAGTGAG       60

CCCCATTGTG TTGTGGTAAA TATGTAGAGG GAGTATAGGG CTGTGACTAG TATGTTGAGT      120

CCTGTAAGTA GGAGAGTGAT ATTTGATCAG GAGAACGTGG TTACTAGCAC AGAGAGTTCT      180

CCCAGTAGGT TAATAGTGGG GGGTAAGGCG AGGTTAGCGA GGCTTGCTAG AAGTCATCAA      240

AAAGCTATTA GTGGGAGTAG AGTTTGAAGC CCTTGAGAGA GGATTATGAT GCGACTGTGA      300

GTGCGTTCGT AGTTTGAGTT TGCTAGGCAG AATAGTAATG AGGATGTAAG TCCGTGGGCG      360

ATTATGAGAA TGACTGCGCC GGTG                                            384

(2) INFORMATION FOR SEQ ID NO:34:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TACTGTGATG TTGTTGCTAT CTTCATCATC TAACACCTGT GATTTTATAT CCATGGTCAC       60

ATATGGAAAA CCCCCAAGGA CAGCCATAAC CTCTTCATAT TTTTCATCTT CAAGGAAGTG      120

CAGTAGAGTG TGACGATCTG ATTCTTTTAA ACTCACCAAA TCCTGGATAG TTTTAATTTT      180

ATACTTCTTA TGATTAGAAA CCCGTCTAAG ATTGTCCTCT TCAATATGAG GGAGCTGCAG      240

AAGGGGAGAC TTAAATTGCT GAAGTCCCTG AACGGCCATC TGAGA                     285

(2) INFORMATION FOR SEQ ID NO:35:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TACTGTGATG TTGTTGCTAT CTTCATCATC TAACACCTGT GATTTTATAT CCATGGTCAC       60

ATATGGAAAA CCCCCAAGGA CAGCCATAAC CTCTTCATAT TTTTCATCTT CAAGGAAGTG      120

CAGTAGAGTG TGACGATCTG ATTCTTTTAA ACTCACCAAA TCCTGGATAG TTTTAATTTT      180

ATACTTCTTA TGATTAGAAA CCCGTCTAAG ATTGTCCTCT TCAATATGAG GGAGCTGCAG      240

AAGGGGAGAC TTAAATTGCT GAAGTCCCTG AACGGCCATC TGAGA                     285
```

(2) INFORMATION FOR SEQ ID NO:36:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
AAGCGGACTT TGGAGGGCAG TGTTATTTTC CCAAAGAAAG ACGGCCAAGG GCAGAGGCAT      60

GGATTCTTTG CAGAGCACTT CCTTTTGGTT TTTCAGTACT GTTTCATAGA CAGTGGGCTC     120

ACATGTTCCT GATAGTGCTG CAGTTGCTTA GAAAGCATCC CAGTTAATTG CAGTAATTAG     180

AACTTCTGGA ATATGCTAGG GCAGAAGTAT GTCAAGTATG TCACATGAAG AAAATGTGAA     240

ATTCAAGAGT AATCCACACG TGAGAAACTA GACAATGTAC ATTCATGTGT TCTCTTGAAA     300

GGAAAGGGAG AGCTGTAAGC TATCGATACC GTC                                 333
```

References

Altschul et al. (1990) Basic local alignment search tool. *J. Mol. Biol.*, 215:403–410.

Braun et al. (1996) *Molecular and Cellular Biology*, 15(8): 4623–4630.

Cregg et al. (1993) Recent Advances in the Expression of Foreign Genes in *Pichia pastoris*. *Bio/Technology* 11:905–910.

Deiss et al. (1996) Cathepsin D protease mediates programmed cell death induced by interferon-γ, Fas/APO-1 and TNF-α. EMBO 15(15):3861–3870.

Deiss et al. (1995) Identification of a novel serine/threonine kinase and a novel 15-kD protein as potential mediators of the γ interferon-induced cell death. *Genes & Develop.* 9:15–30.

Deiss and Kimchi (1991) A Genetic Tool Used to Identify Thioredoxin as a Mediator of a Growth Inhibitory Signal. *Science* 252:117–120.

Diatchenko et al. (1996) *Proc. Natl. Acad. Sci. USA.*, 93:6025–6030.

Gilboa et al. (1986) Transfer and expression of cloned genes using retroviral vectors. *BioTechniques* 4(6):504–512.

Gubler and Hoffman (1983) *Gene (Amst.)* 25:263.

Gudkov et al. (1994) Cloning mammalian genes by expression selection of genetic suppressor elements: association of kinesin with drug resistance and cell immortalization. *Proc. Natl. Acad. Sci. U.S.A.*, 91:3744–3748.

Hirt (1967) Selective extraction of polyoma DNA from infected mouse cell cultures. *J. Mol. Biol.*, pp. 365–9.

Holzmayer et al. (1992) Isolation of dominant negative mutants and inhibitory antisense RNA sequences by expression selection of random DNA fragments. *Nucleic Acids Res.*, 20:711–717.

Izant and Weintraub (1984) Inhibition of thymidine kinase gene expression by anti-sense RNA: a molecular approach to genetic analysis. *Cell*, 36: 1007–1015.

Kissil et al. (1995) "Isolation of DAP3, a Novel Mediator of Interferon-γ-induced Cell Death" *J. Biol. Chem.* 270(46): 27932–27936.

Levy-Strumpf et al. (1997) DAP-5, a novel homolog of eukaryotic translation initiation factor 4G isolated as a putative modulator of gamma interferon-induced programmed cell death. *Mol. Cell. Biol.*, 17:1615–1625.

Li and Cohen (1996) Tsg101: A novel tumor susceptibility gene isolated by controlled homozygous functional knockout of allelic loci in mammalian cells. *Cell*, 85:319–329.

Meissner et al. (1987) *PNAS (USA)* 84:4171.

Roninson et al. (1995) Genetic suppressor elements: new tools for molecular oncology—thirteenth Cornelius P. Rhoads Memorial Award Lecture. *Cancer Res.*, 55:4023–4028.

Schena et al., 1995, Aiello et al., 1994, Shen et al., 1995, Bauer et al., 1993, Liang and Pardee, 1992, Liang and Pardee, 1995, Liang et al., 1993, Braun et al., 1995, Hubank and Schatz, 1994

Smith et al. (1995) genetic footprinting: a genomic strategy for determining a gene's function given its sequence. PNAS 92:6479–6489.

Su et al. (1993) LYAR, a novel nucleolar protein with zinc finger DNA-binding motifs, is involved in cell growth regulation. *Genes Dev.*, 7:735–748.Schena et al. (1995) *Science*, 270:467–470.

Agrawal, 1996. Antisense oligonucleotides: towards clinical trials, TIBTECH, 14:376.

Calabretta, et al, 1996. Antisense strategies in the treatment of leukemias. Semin. Oncol. 23:78.

Crooke, 1995. Progress in antisense therapeutics, Hematol. Pathol. 2:59.

Feigner, 1997. Nonviral Strategies for Gene Therapy. Scientific American. June, 1997, pgs 102–106.

Gewirtz, 1993. Oligodeoxynucleotide-based therapeutics for human leukemias, Stem Cells Dayt. 11:96.

Hanania, et al 1995. Recent advances in the application of gene therapy to human disease. Am. J. Med. 99:537.

Lefebvre-d'Hellencourt et al, 1995. Immunomodulation by cytokine antisense oligonucleotides. Eur. Cytokine Netw. 6:7.

Lev-Lehman et al., 1997. Antisense Oligomers in vitro and in vivo. In *Antisense Therapeutics*, A. Cohen and S. Smicek, eds (Plenum Press, New York)

Loke et al, 1989. Characterization of oligonucleotide transport into living cells. PNAS USA 86:3474.

Wagner et al., 1996. Potent and selective inhibition of gene expression by an antisense heptanucleotide. Nature Biotechnology 14:840–844.

Wagner, 1994. Gene inhibition using antisense oligodeoxynucleotides. Nature 372:333.

Radhakrishnan et al., 1990. The automated synthesis of sulfur-containing oligodeoxyribonucleotides using 3H-1, 2-Benzodithiol-3-One 1,1 Dioxide as a sulfur-transfer reagent. J. Org. Chem. 55:4693–4699.

What is claimed is:

1. A method for the identification of genes that are essential for the maintenance of specific cell phenotypes including the steps of:
   a) identifying a cell type with a phenotype of interest;
   b) inactivating genes in the cell type of interest with a gene inactivation means on an aliquot of a culture of the cell type;
   c) applying positive selection means to an aliquot of the cell culture of step b;
   d) isolating the selected cells of step c which continue to maintain the phenotype following gene inactivation; and
   e) utilizing subtraction analysis means to identify the gene in the cells not isolated in step c which have been inactivated that affects the phenotype of interest.

2. The method as set forth in claim 1 wherein said gene inactivation means are performed using a Technical Knock Out (TKO) inactivation.

3. The method as set forth in claim 1 wherein the phenotype of interest can be selected from the group consisting of phenotypes relating to growth, phenotypes relating to release of factors and phenotypes relating to cell functions.

4. The method as set forth in claim 1 wherein the positive selection means can be selected from the group consisting of ability of cells to survive under specific culture conditions, ability to express a specific factor, changes in cell structure, and differential gene expression.

5. The method as set forth in claim 1 wherein the subtraction analysis means are selected among the methods of differential display, representational differential analysis (RDA), suppressive subtraction hybridization (SSH), serial analysis of gene expression (SAGE), gene expression microarray (GEM), nucleic acid chip technology, or direct sequencing.

6. A method for the identification of genes that are essential for the maintenance of specific cell phenotypes including the steps of:
   a) identifying a cell type with a phenotype of interest;
   b) preparing an expression cDNA library from cells expressing the phenotype;
   c) transfecting a cell culture of the cell type with anti-sense expression vectors incorporating the expression cDNA library;
   d) applying positive selection means to an aliquot of the transfected cell culture and reserving an untreated aliquot;
   e) observing cells which continue to maintain the phenotype and isolating the antisense expression vector from the cells maintaining the phenotype;
   f) identifying anti-sense expression vectors that are present in the reserved aliquot and not in cells maintaining the phenotype by subtraction means whereby anti-sense expression vectors are identified that have targeted genes that maintain the phenotype.

7. The method as set forth in claim 6 wherein the step of recloning and sequencing the antisense expression vectors that target the genes that maintain the phenotype is performed on the identified antisense expression vectors.

* * * * *